United States Patent
Hechler et al.

(10) Patent No.: US 7,253,308 B1
(45) Date of Patent: *Aug. 7, 2007

(54) METHOD FOR CATALYTIC PHASE OXIDATION TO (METH) ACROLEIN AND/OR (METH) ACRYLIC ACID

(75) Inventors: Claus Hechler, Ludwigshafen (DE); Otto Machhammer, Mannheim (DE); Gerhard Olbert, Dossenheim (DE); Uwe Stabel, Otterstadt (DE); Peter Zehner, Ludwigshafen (DE)

(73) Assignee: BASF Actiengesellschaft, Ludwigshafen (DE)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 655 days.

(21) Appl. No.: 10/110,229

(22) PCT Filed: Nov. 3, 2000

(86) PCT No.: PCT/EP00/10851

§ 371 (c)(1), (2), (4) Date: Apr. 22, 2002

(87) PCT Pub. No.: WO01/32301

PCT Pub. Date: May 10, 2001

(30) Foreign Application Priority Data

Nov. 3, 1999 (DE) .............................. 199 52 964

(51) Int. Cl.
*C07C 51/16* (2006.01)
*C07B 41/00* (2006.01)

(52) U.S. Cl. .................... 562/532; 562/545; 568/469.9
(58) Field of Classification Search ............... 562/512, 562/512.2, 523, 542, 544, 545, 549, 598; 568/448–497
See application file for complete search history.

(56) References Cited

U.S. PATENT DOCUMENTS

| | | | |
|---|---|---|---|
| 3,918,469 A | * | 11/1975 | Zamboni et al. ............... 137/5 |
| 4,203,906 A | * | 5/1980 | Takada et al. ............... 549/248 |
| 4,544,544 A | | 10/1985 | Le Page et al. |
| 5,510,558 A | | 4/1996 | Umansky et al. |

FOREIGN PATENT DOCUMENTS

| | | |
|---|---|---|
| CN | 1105352 | 11/1994 |
| DE | 1962431 | 6/1970 |
| DE | 20 16 614 | 10/1971 |
| DE | 197 54 185 | * 12/1997 |
| DE | 197 19 375 | 11/1998 |
| DE | 19754185 | 2/1999 |
| DE | 197 53 720 | 6/1999 |

(Continued)

*Primary Examiner*—Karl Puttlitz
(74) *Attorney, Agent, or Firm*—Oblon, Spivak, McClelland, Maier & Neustadt, P.C.

(57) ABSTRACT

A process for the continuous gas-phase oxidation of $C_3$- and $C_4$-precursors to (meth)acrolein and/or (meth)acrylic acid in the presence of a catalyst in a reactor which has a feed for the reaction mixture at one reactor end and removal of the reaction mixture at the opposite reactor end and which is equipped with means, arranged in the interior of the reactor, for removing the heat of reaction, through which means a heat exchange composition flows and which means are in the form of heat exchanger plates, is proposed.

30 Claims, 8 Drawing Sheets

FOREIGN PATENT DOCUMENTS

| | | | |
|---|---|---|---|
| DE | 19754185 | * | 10/1999 |
| DE | 19907316 | * | 8/2000 |
| DE | 100 31 347 | | 1/2001 |
| EP | 0 092 097 | | 1/1985 |
| EP | 0 253 409 | | 7/1987 |
| EP | 0 976 446 | | 2/2000 |

* cited by examiner

METHOD FOR CATALYTIC PHASE OXIDATION TO (METH) ACROLEIN AND/OR (METH) ACRYLIC ACID

The present invention relates to a process for the continuous gas-phase oxidation to (meth)acrolein and/or (meth)acrylic acid. Below, the term (meth)acrolein represents acrolein or methacrolein and analogously (meth)acrylic acid designates the substances acrylic acid or methacrylic acid.

(Meth)acrolein and (meth)acrylic acid are key chemicals.

The known industrial processes for the gas-phase oxidation to (meth)acrolein and/or (meth)acrylic acid (for example according to DE-A-196 24 31) are carried out as a rule in tube-bundle reactors which have a large number of reaction tubes, currently up to 28 000, welded in between tube sheets. Here, preferably temperatures of from 200 to 450° C. and, if required, superatmospheric pressure are employed. The reaction tubes are filled with the heterogeneous oxidation catalysts and reaction mixture flows through said tubes. A heat-exchange composition, as a rule a salt melt, frequently a mixture of potassium nitrate, sodium nitrite and sodium nitrate, which removes the heat of reaction, flows through the interior of the reactor, between the reaction tubes.

Such salt melts can be used at from about 200 to 480° C. without pressure, under hydrostatic pressure, as a primary heat transfer medium for removing heat. The salt is heated between reactor entrance and reactor exit, as a rule on average by about 2° C. By generating steam with a pressure of from about 20 to 60 bar, the salt is recooled in a secondary cooling circulation to the feed temperature. In order to achieve a good heat transfer coefficient by a sufficiently high flow rate of the salt around the tubes, the salt in the reactor is passed crosswise relative to the tubes with repeated deflection and countercurrently to the reaction gas. As a result, radial temperature differences of up to 7° C. are present in the salt melt in the reactor.

The temperature regulation of the reactor is effected by means of the salt inlet temperature which, in order to avoid total oxidation, must be chosen sufficiently low for the desired, regular reaction still to take place optimally at the point of the highest temperature in the reactor, the hotspot.

Such reactors thus have, on the one hand, the disadvantage that, owing to the radial flow of the heat exchange composition, no isothermicity can be achieved over the reactor cross section but there are always radial temperature differences in the salt melt between the reaction tubes located toward the inside and reaction tubes located further outside. This has adverse effects, particularly in the hotspot region, with the result that the maximum temperature at which the reactor as a whole can be operated has to be limited, necessitating high flow rates of heat exchange composition.

The further disadvantage is that the diameter of the tube-bundle reactors has a technical upper limit owing to the dimensions and weight of the tube sheets. The capacity of the plant can thus be increased only by increasing the reactor length. With increasing height of the catalyst bed in the reactor tubes, however, the pressure drop increases with disadvantageous effects on the selectivity.

The known process in tube-bundle reactors has the further disadvantage that, owing to the temperature inhomogeneities, the selectivity decreases sharply at very high conversions. On the other hand, in order to achieve a high yield as a whole, it is desirable to operate all reaction tubes uniformly at optimum conversion and selectivity.

Deposits of byproducts on the catalyst result in tubes located toward the outside having a large pressure drop in the course of operation. This results in nonuniform flow through the tubes, which causes lower conversion rates in the outer tubes. In addition to the decrease in conversion in these tubes located toward the outside, there is greater flow through the tubes located toward the inside, so that the pressure drop there increases and the yield decreases. Even if deposits are present only at the beginning of a tube, the reaction rate of the catalyst bed is adversely affected over the total tube length.

DE-C-197 54 185 describes, for example, a reactor having a cylindrical reactor container, heat exchanger plates in the form of thermal sheet metal plates in the reactor container being arranged vertically side by side on the perforated bottom of the reactor, a specified distance apart. A cooling medium flows through the plates and is fed to the heat exchanger plates in the region of the top container via suitable means and is removed from the heat exchanger plates in the region of the bottom of the container via suitable means. Between the heat exchanger plates, a gaseous reaction medium is passed countercurrently to the cooling medium, with feeding in the region of the bottom of the container and removal in the region of the top of the container. However, the publication does not indicate that such a reaction can be particularly advantageously used for the catalytic gas-phase oxidation to (meth)acrolein and/or (meth)acrylic acid, in particular the selectivity of the reaction to give the respective main product being improved compared with the reaction being carried out in a tube-bundle reactor.

DE-A-197 19 375 describes a process for the preparation of ethylene oxide by catalytic gas-phase oxidation of ethylene with oxygen in a reactor, the catalyst being arranged in reaction zones between heat exchanger plates and gaseous reaction mixture flowing through said catalyst. In the catalytic gas-phase oxidation to ethylene oxide, a comparatively small quantity of heat is involved per unit volume of catalyst.

It is an object of the present invention to provide a process for the preparation of (meth)acrolein and/or (meth)acrylic acid, which has high cost-efficiency, in particular with respect to the cost of heat exchange composition, and has improved selectivity also at very high conversions and in plants having a large capacity.

We have found that this object is achieved by a process for the continuous gas-phase oxidation of $C_3$- or $C_4$-precursors to (meth)acrolein and/or (meth)acrylic acid in the presence of a catalyst in a reactor with a feed for the reaction mixture at one reactor end and removal at the opposite reactor end and with means, arranged in the interior of the reactor, for removing the heat of reaction, through which means a heat exchange composition flows.

In said process, the means are heat exchanger plates.

Surprisingly, it has been found that, in spite of the substantially higher heat evolution per unit volume of catalyst compared with the ethylene oxide preparation and the considerable hotspot problem, which is of minor importance in the ethylene oxide preparation, the catalytic gas-phase oxidation to (meth)acrolein and/or (meth)acrylic acid can be carried out in a reaction space between heat exchanger plates and hence a catalyst bed extending in two dimensions over the reactor cross section, and the reaction nevertheless remains controllable. An unforeseeable increase in selectivity with respect to the formation of (meth)acrolein and/or (meth)acrylic acid was achieved thereby.

In principle, all suitable $C_3$- or $C_4$-starting materials, in particular $C_3$- or $C_4$-alkanes, $C_3$- or $C_4$-alkenes, $C_3$- or $C_4$-alkanols and/or $C_3$- or $C_4$-alkanols and/or intermediates thereof, particularly advantageously of propene, acrolein, tert-butanol, isobutane, isobutene, isobutylaldehyde, methacrolein, isobutyric acid or methyl tert-butyl ether, can be prepared as starting compounds. Furthermore, all intermediates of said compounds in which the actual $C_3/C_4$ starting compound is formed only as an intermediate during the gas-phase oxidation can be used. An example for the preparation of methacrylic acid is methyl tert-butyl ether or isobutyric acid.

The catalytic gas-phase reaction of propene and/or acrolein to acrylic acid with molecular oxygen is particularly advantageous.

Here, temperatures of from 200 to 450° C. and, if required, superatmospheric pressure are preferably employed. Preferably used heterogeneous catalysts are oxidic multicomponent catalysts based on the oxides of molybdenum, bismuth and iron in the 1 st stage (oxidation of propene to acrolein) and the oxides of molybdenum and vanadium in the 2nd stage (oxidation of acrolein to acrylic acid). If propane is used as a starting material, it can be converted into a propene/propane mixture by catalytic oxydehydrogenation, as described in U.S. Pat. No. 5,510,558, by homogeneous oxydehydrogenation, according to CN-A-1 105 352, or by catalytic dehydrogenation, as described in EP-A-0 253 409. When a propene/propane mixture is used, propane acts as a diluent gas. Suitable propene/propane mixtures are also refinery propene (70% of propene and 30% of propane) or cracker propene (95% of propene and 5% of propane). In principle, propene/propane mixtures such as the abovementioned ones can be oxidized with oxygen or air or a mixture of oxygen and nitrogen of any composition to give acrolein and acrylic acid.

The catalytic gas-phase oxidation gives not pure acrylic acid but a gaseous mixture which, in addition to the acrylic acid, may contain substantially unconverted acrolein and/or propene, steam, carbon monoxide, carbon dioxide, nitrogen, propane, oxygen, acetic acid, propionic acid, formaldehyde, further aldehydes and maleic anhydride as secondary components. Usually, the reaction product mixture contains from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic anhydride and from 20 to 98, preferably from 50 to 98, % by weight of inert diluent gases, based in each case on the total reaction mixture. In particular, saturated $C_1$–$C_6$-hydrocarbons, such as from 0 to 90% by weight of methane and/or propane, as well as from 1 to 30% by weight of steam, from 0.05 to 15% by weight of oxides of carbon and from 0 to 90% by weight of nitrogen, based in each case on 100% by weight of diluent gas, are present as inert diluent gases.

Methacrylic acid can be prepared analogously to acrylic acid by catalytic gas-phase reaction of $C_4$ starting compounds with molecular oxygen. Particularly advantageously, methacrylic acid is obtainable, for example, by catalytic gas-phase oxidation of isobutene, isobutane, tert-butanol, isobutylaldehyde, methacrolein or methyl tert-butyl ether. Catalysts used are likewise transition metal mixed oxide catalysts (e.g. Mo, V, W and/or Fe). Particularly suitable processes are those in which the preparation is effected starting from methacrolein, in particular when the methacrolein is produced by gas-phase catalytic oxidation of tert-butanol, isobutane or isobutene or by reaction of formaldehyde with propionaldehyde according to EP-B-0 092 097. Thus, it is also possible to prepare methacrylic acid in two stages by (1) condensation of propionaldehyde with formaldehyde (in the presence of a secondary amine as the catalyst) to give methacrolein and (2) subsequent oxidation of the methacrolein to methacrylic acid.

As in the case of the preparation of acrylic acid, it is not pure methacrylic acid which is obtained but a gaseous mixture which, in addition to methacrylic acid, may contain substantially unconverted methacrolein and/or steam, carbon monoxide, carbon dioxide, nitrogen, oxygen, acetic acid, propionic acid, further aldehydes and maleic anhydride as secondary components. The novel process is used in particular when the reaction mixture contains from 0.02 to 2% by weight, based on the total reaction mixture, of methacrolein and otherwise substantially the same corresponding components as in the preparation of acrylic acid.

The shape of the reactor is in principle not subject to any restrictions; conventional cylindrical reactors but also right parallelepiped reactors may be used.

There are also no restrictions with respect to the orientation of the reactors; the reactors can in principle be oriented in any position, vertical orientation generally being preferred for the special case of the cylindrical reactors.

According to the invention, reactors which are equipped with heat exchanger plates are used for the process for the continuous gas-phase oxidation to (meth)acrolein and/or (meth)acrylic acid.

Heat exchanger plates are predominantly extensive structures which have an interior provided with feed and removal lines and have a small thickness in relation to the area. They are produced as a rule from metal sheets, frequently from steel sheets. Depending on the application, in particular on the properties of the reaction medium and on the heat exchange composition, however, special, in particular corrosion-resistant, materials may be used. The feed or removal means for the heat exchange composition are as a rule arranged at opposite ends of the heat exchanger plates; in the case of the reactors having heat exchanger plates for carrying out reactions with high heat evolution, it being possible for said reactions to be both exothermic and endothermic reactions.

There are no basic restrictions with regard to heat exchange compositions which can be used in the novel process. Both inorganic and organic liquid heat exchange compositions which remain in the liquid state or partly or completely vaporize at the reaction temperature of the catalytic gas-phase oxidation may be used. For example, it is possible to use heat transfer oils or salt melts as a heat exchange composition; however, this information in no way restricts the choice of the heat exchange composition which may be used.

Here, it is particularly advantageous to use a heat exchange composition which at least partially vaporizes at the reaction temperature of the catalytic gas-phase oxidation. Water is particularly preferred for this purpose. By utilizing evaporative cooling, efficient heat removal is ensured here, a substantial reduction in the required amount being achieved for the removal of the same quantity of heat compared with the use of a heat exchange composition which does not change its state of aggregation.

When the catalyst is arranged in a bed around the heat exchanger plates, it is advantageous, in the case of local constrictions, if the reaction gas can be distributed again over the full catalyst cross section between two heat exchanger plates after flowing past the constriction and the total reaction cross section can contribute to the conversion.

Evaporative cooling can be effected by both the cocurrent and the countercurrent method. During cocurrent operation with flow from below, it is additionally possible to regulate the level of the boiling liquid so that there is less heat removal toward the end of the reaction tubes and the total yield is increased as a result of the now higher temperature level there.

In evaporative cooling, a defined vapor pressure is established on the cooling medium side depending on the temperature (in the case of water, from about 20 to 120 bar), so that a correspondingly pressure-resistant design of the cooling medium side of the apparatus is required.

According to the invention, the reaction mixture is fed at one reactor end to the interior of the reactor, between the heat exchanger plates, and is removed at the opposite reactor end. The reaction mixture thus flows through the reactor through the intermediate space between the heat exchanger plates. There is thus continuous cross-mixing of the reaction mixture, resulting in high homogeneity thereof. For a given conversion, a substantially better selectivity can thus be achieved compared with a procedure which does not ensure cross-mixing, as is the case, for example, when the reaction is carried out in the reaction tubes of a tube-bundle reactor.

There are in principle no restrictions with regard to the arrangement of the heat exchanger plates in the reactor; the heat exchanger plates can be arranged, for example, spirally, concentrically or radially in the reactor.

A cocurrent flow of heat exchange composition and reaction mixture through the reactor is particularly preferred. This ensures better adaptation to the temperature profile of the reaction, with a hotspot at an early stage of the reaction.

Particularly advantageously used heat exchanger plates are those which are wedge-shaped, i.e. whose interior through which the heat exchange composition flows preferably decreases continuously in the direction of flow of the reaction mixture. Such wedge-shaped heat exchanger plates can be produced, for example, by placing two metal sheets one on top of the other and welding them with increasing spacings. The plates are then clamped in a slightly inclined inflation apparatus and are inflated to a predetermined spacing.

By means of wedge-shaped heat exchanger plates, the adaptation to the temperature profile of the reaction can be optimized.

In a further advantageous embodiment, the heat exchanger plates can be completely or partially welded lengthwise. For this purpose, in each case two metal sheets are placed one on top of the other, welded by roller seam welding over longitudinal seams and inflated by means of a suitable inflation apparatus.

According to a further embodiment, flat, rectangular metal sheets oriented parallel to one another are introduced into the interior of the reactor, substantially completely filling said interior, in each case two opposite sides on each metal sheet being bent over at right angles in the same direction and, in the respective subsequent metal sheet, the other two sides opposite one another being bent over at right angles in the same direction by the same distance, so that in each case right parallelepiped spaces form, the reaction mixture or the heat exchange composition flowing transversely through the respective adjacent spaces.

According to a further embodiment, the heat exchanger plates are arranged parallel to one another in the longitudinal direction of the reactor.

The catalyst may be introduced in the form of catalyst moldings into the intermediate space between the heat exchanger plates. The introduction and the changing of the catalyst bed is simpler and more uniform compared with filling into the reaction tubes with a tube-bundle reactor. Larger associated reaction spaces form and there is less danger of blockage of the catalyst bed. This leads to uniform conversions and hence higher selectivity.

It is however also possible, additionally or alternatively to the catalyst bed, to coat the heat exchanger plates catalytically on their outsides over which the reaction mixture flows. Owing to the substantially flat form of the heat exchanger plates, the latter can be coated more easily compared with the reaction tubes.

According to a further preferred embodiment, two or more reaction zones having separate circulations of heat exchange composition can be arranged in the direction of flow of the reaction mixture. Such a process variant is particularly suitable for the two-stage oxidation of the $C_3$ starting material to acrolein in a first process stage with removal of the heat of reaction via a first stack of heat exchanger plates, intermediate cooling via a second stack of heat exchanger plates and finally in the second oxidation stage to acrylic acid and heat removal via a third stack of heat exchanger plates. It is however also possible to carry out the two-stage oxidation to acrylic acid in one apparatus having only two stacks of heat exchanger plates, dispensing with the intermediate cooling.

The novel process thus has the advantage that, by using cooling surfaces with an external catalyst bed, the cooling medium can be fed cocurrently with or countercurrently to the reaction gas. Consequently, a uniform temperature distribution is achieved in the individual reactor cross sections in the total reactor, so that the hotspot temperature is identical over the total reactor cross section, which leads to an improved yield.

The process variant comprising cooling by the cocurrent method is particularly advantageous because the temperature of the cooling medium is still low on reaching the hotspot and the cooling is thus very effective, with the result that the quantity of coolant to be circulated by pumping can be considerably reduced.

The further process variant, in which a boiling liquid, in particular water, is used as a cooling medium, has additional advantages: the heat removal is considerably improved and, with the use of water, additionally no secondary cooling medium is required.

The heat exchanger plates can preferably be combined into two or more modules. The modules should be arranged in such a way that the reactor cross section is filled very substantially uniformly. They may be of different geometric forms but are preferably of geometric forms identical to one another, preferably of wedge-shaped geometry. The modular design is particularly advantageous for large reactors since, for manufacturing reasons, the maximum available width of individual heat exchanger plates is limited. This limitation can be overcome by forming a plurality of plate modules. Another advantage is that the plate modules are individually replaceable and that specific catalyst change in individual modules is possible.

The novel solution particularly advantageously permits high-load operation in the process for the continuous gas-phase oxidation to (meth)acrolein and/or (meth)acrylic acid. According to the invention, the heat of reaction is removed by a heat exchange composition flowing in heat exchanger plates. Heat exchanger plates can be arranged relatively close to one another. With decreasing plate spacing, in the range of from about 10 to 30 mm, preferably from 15 to 20 mm, the reaction medium can be better cooled, the heat removal is improved and the hotspot is reduced, with the result that the throughput and hence the loading of the reactor can be increased compared with a conventional tube-bundle reactor.

BRIEF DESCRIPTION OF THE DRAWINGS

The invention is explained in more detail below with reference to a drawing.

In the figures, identical or corresponding features are provided with identical reference numerals.

Figure 1:
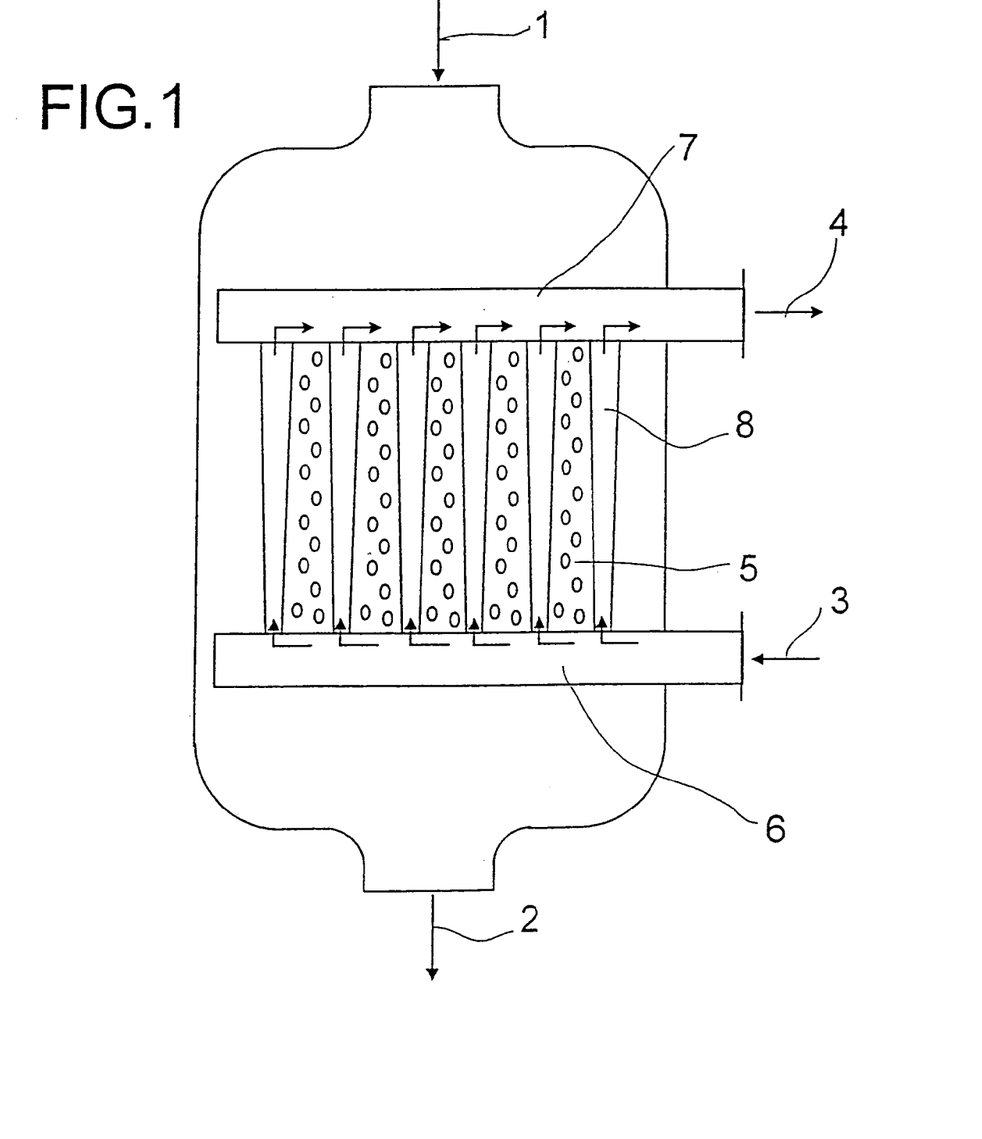
FIG. 1 shows, in longitudinal section, a particularly preferred embodiment of a reactor which is particularly suitable for carrying out the process.
Figure 1A:
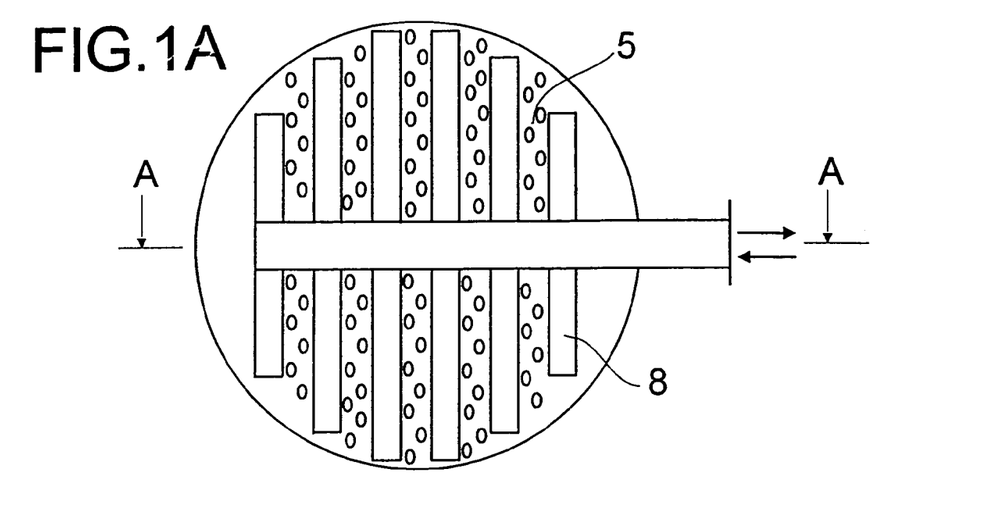
FIG. 1A shows a cross section through the reactor from FIG. 1.

The reactor shown in longitudinal section in FIG. 1 has the shape of a cylinder with feeding of the reaction mixture 1 in the upper region and removal of the reaction mixture 2 in the lower reactor region. The preferably gaseous reaction mixture itself is denoted by 5. Heat exchanger plates 8 which have the particularly preferred wedge-shaped formation are arranged in the interior of the reactor, in the longitudinal direction thereof. A heat exchange composition flows through the reactor plates and is introduced via a feed 3 and a distributor line 6 and removed via a collecting line 7 and a removal line 4. The cross section in FIG. 1A illustrates the substantially parallel arrangement of the heat exchanger plates 8.

Figure 1B:
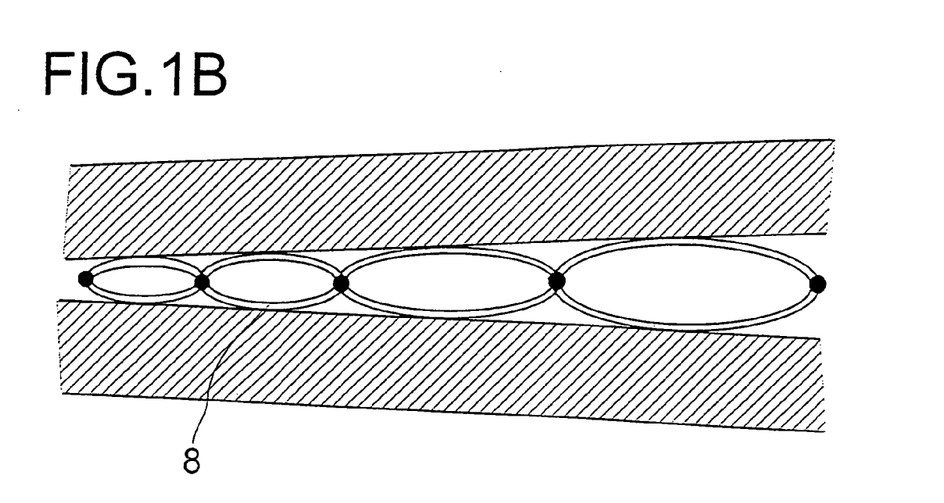
FIG. 1B shows a longitudinal section through a heat exchanger plate of the reactor from FIG. 1.
Figure 1C:
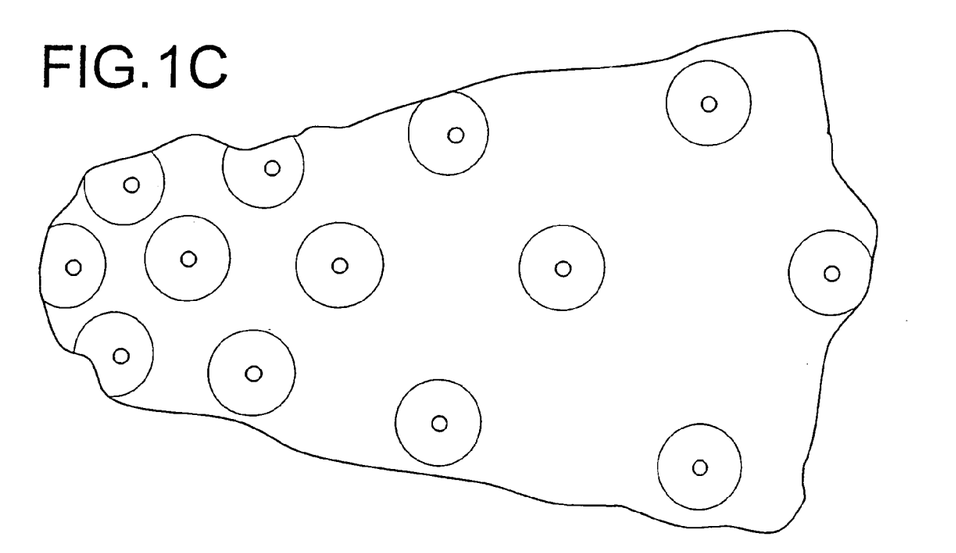
FIG. 1C shows a preferred arrangement of the welding points of the heat exchanger plate from FIG. 1B.

FIGS. 1B and 1C clearly show the preferred wedge-shaped formation of the heat exchanger plates 8 and their formation by metal sheets spot-welded to one another.

Figure 2:
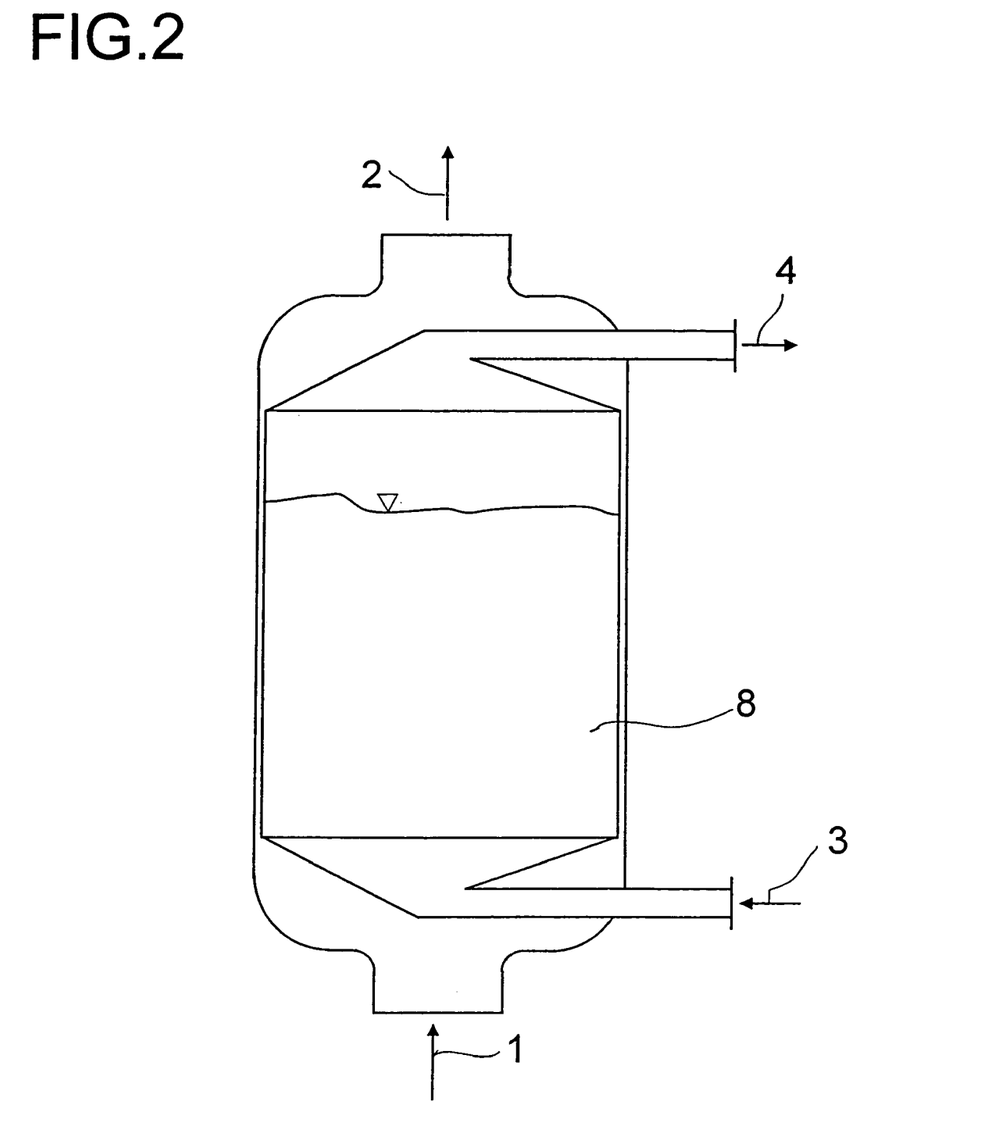
FIG. 2 shows a longitudinal section through a reactor particularly suitable for carrying out the process and having cocurrent flow of reaction mixture and heat exchange composition.

FIG. 2 shows, by way of example, a longitudinal section through a reactor having cocurrent flow of the reaction mixture and heat exchange composition. FIG. 2 clearly shows that, in the heat exchanger plates 8, the liquid level of the heat exchange composition ranges only to a specific height, i.e. the heat exchange composition vaporizes above this. The heat removal thus takes place through evaporative cooling.

Figure 3:
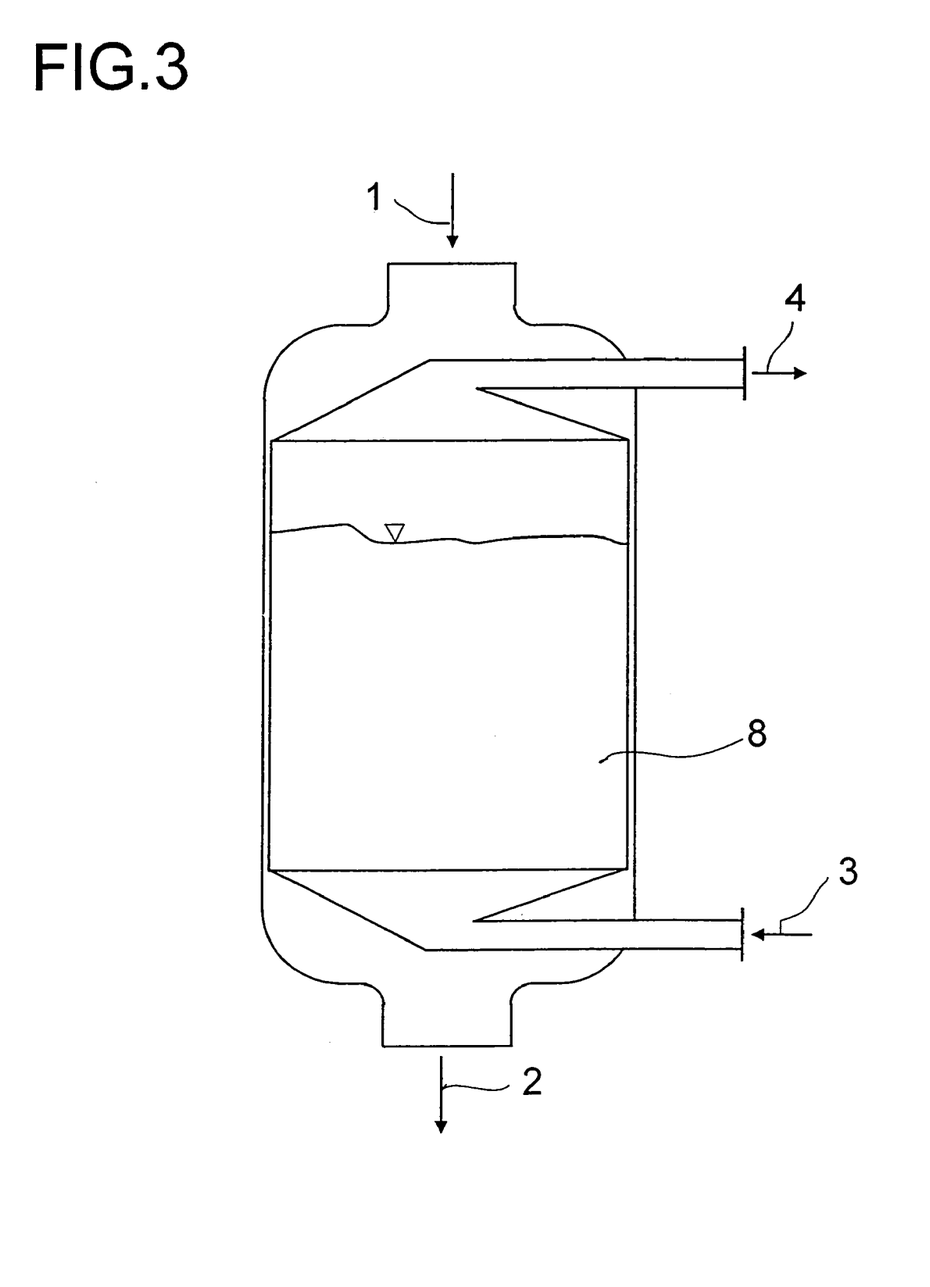
FIG. 3 shows a longitudinal section through a further preferred embodiment of a reactor particularly suitable for carrying out the process and having countercurrent flow of reaction mixture and heat exchange composition.

FIG. 3 shows, by way of example, countercurrent flow of reaction mixture and heat exchange composition.

Figure 4:
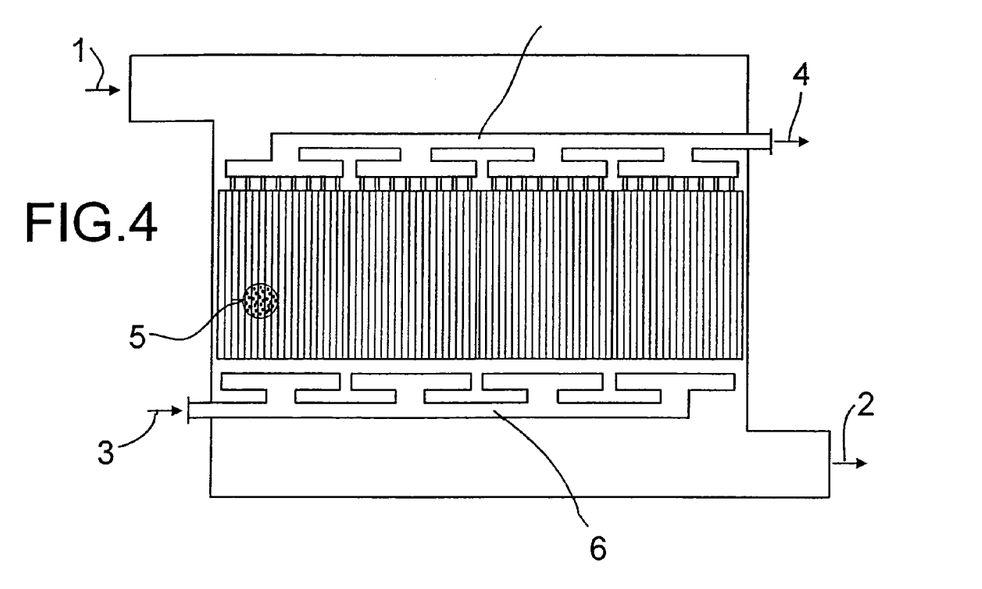
FIG. 4 shows a longitudinal section through a right parallelpiped reactor.
Figure 4A:
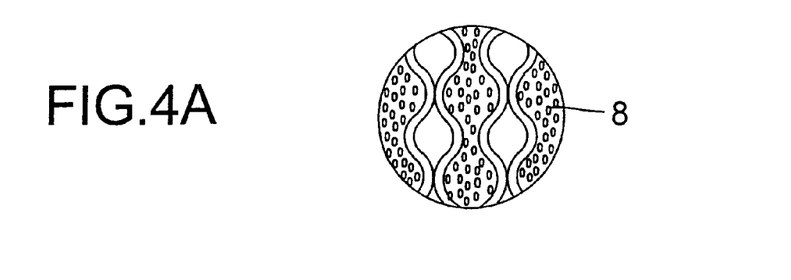
FIG. 4A shows an enlarged section of the reactor shown in FIG. 4, for illustrating the design of the reactor plates.
Figure 4B:
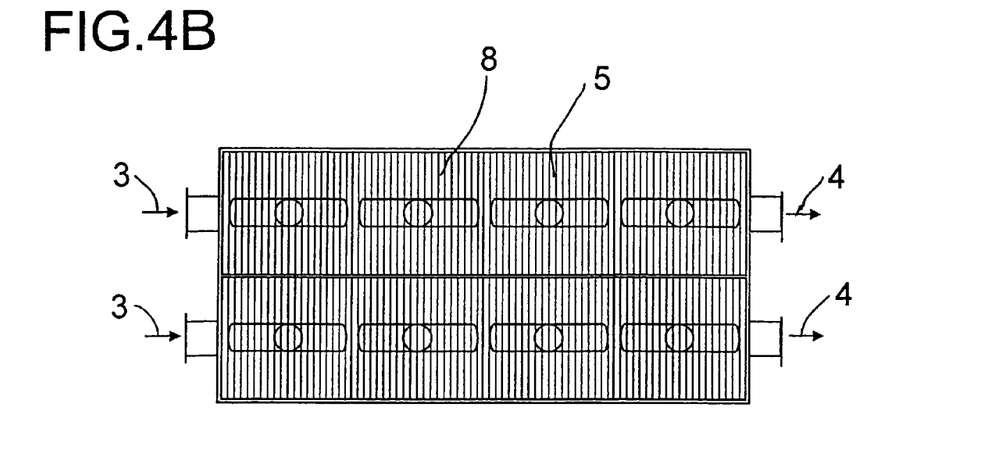
FIG. 4B shows a cross section through the reactor shown in FIG. 4

FIG. 4 shows a longitudinal section through a right parallelepiped reactor; the formation of the heat exchanger plates (8) is clearly shown enlarged in the section shown in FIG. 4A. FIG. 4B shows a cross section through the right parallelepiped reactor shown in FIG. 4.

Figure 5:
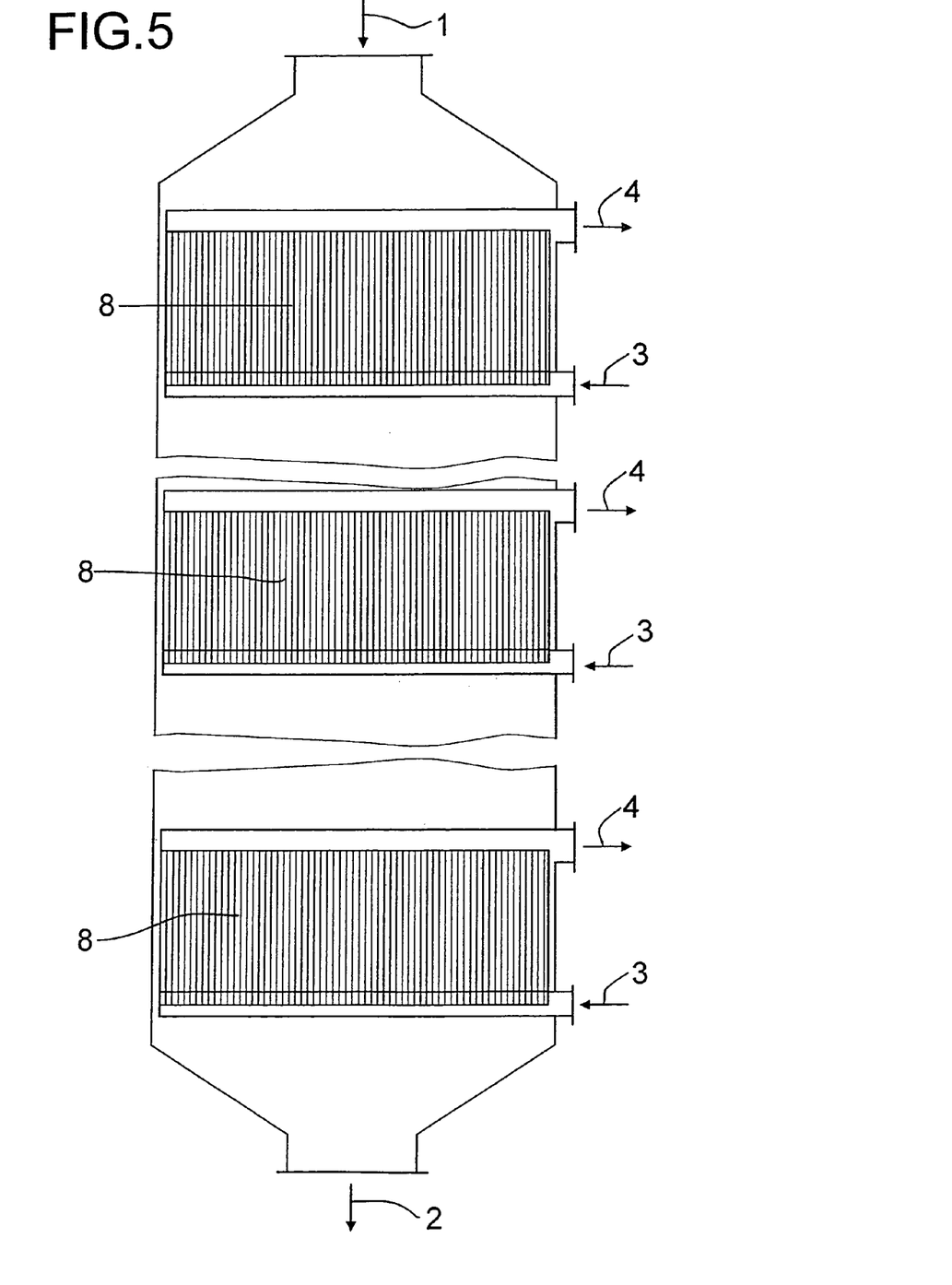
FIG. 5 shows a longitudinal section through a reactor which has three reaction zones by way of example.

The reactor shown in longitudinal section in FIG. 5 has, by way of example, three reaction zones, each having separate circulations of heat exchange composition.

Figure 6A:
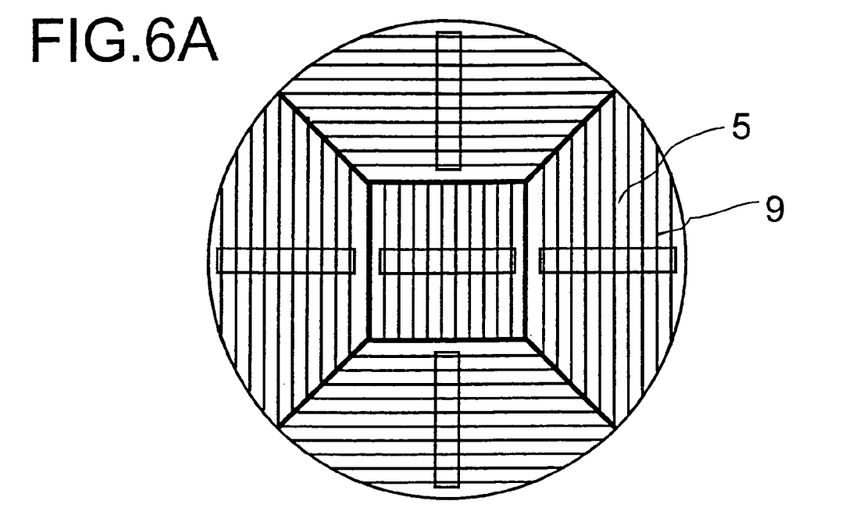
FIG. 6A shows a cross section through a reactor having five modules of heat exchanger plates and FIG. 6B shows a longitudinal section through the reactor shown in cross section in FIG. 6A.
Figure 6B:
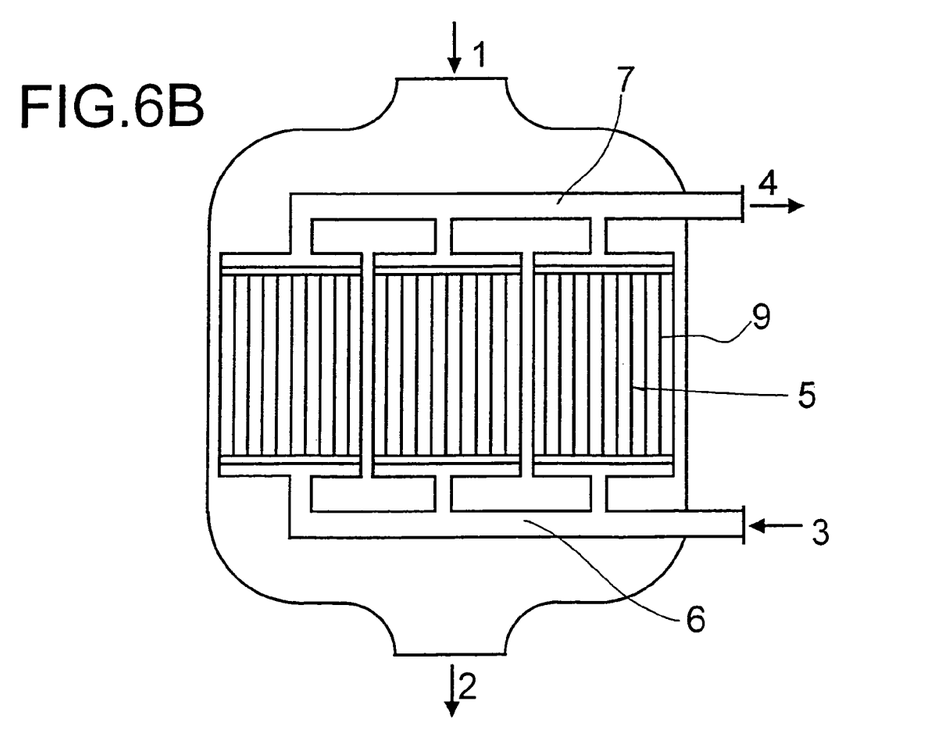

The reactor shown in cross section in FIG. 6A and in longitudinal section in FIG. 6B has, by way of example, five groups of heat exchanger plates 8 which are combined into modules 9. The diagram in FIG. 6A shows that the cross section is substantially uniformly filled with heat exchanger plates.

We claim:

1. A process for making (meth)acrolein or (meth)acrylic acid comprising:
   continuously oxidizing in a gas phase a $C_3$ or $C_4$ precursor in the presence of a catalyst under conditions suitable for the formation of (meth)acrolein or (meth)acrylic acid;
   wherein said oxidizing takes place in a reactor with a feed for the $C_3$ or $C_4$ precursor reaction mixture at one end and for removal of the reaction mixture at the opposite end of the reactor,
   wherein heat exchanger plates are arranged in the interior of said reactor, and through which plates a heat exchange composition flows for the removal of the heat generated by said oxidation,
   wherein heat generated by the oxidation is transferred into the heat exchanger plate and then into the heat exchange composition contained inside of the heat exchanger plate, and
   wherein said heat is removed by evaporative cooling of the heat exchange composition under super atmospheric pressure.

2. The process of claim 1, comprising cocurrent flow of the reaction mixture and the heat exchange composition.

3. The process of claim 1, wherein said reactor comprises heat exchanger plates with a wedge-shaped formation and through the interiors of which plates a heat exchange composition flows.

4. The process of claim 3, wherein the heat exchange flow decreases continuously in the direction of cocurrent flow of the reaction mixture.

5. The process of claim 1, wherein the heat exchanger plates are formed from metal sheets which are completely or partially longitudinally welded or spot-welded to one another.

6. The process of claim 1, wherein flat, rectangular metal sheets oriented parallel to one another are introduced into the interior of the reactor, substantially completely filling said interior, in each case two opposite sides on each metal sheet being bent over at right angles in the same direction and, in the respective subsequent metal sheet, the other two sides opposite one another being bent over at right angles in the same direction by the same distance so that in each case right parallelepiped spaces form, the reaction mixture or the heat exchange composition flowing transversely through the respective adjacent spaces.

7. The process of claim 1, wherein the heat exchanger plates are arranged parallel to one another.

8. The process of claim 1, wherein the surfaces of the heat exchanger plates which face the reaction mixture are completely or partially catalytically coated.

9. The process of claim 1, comprising two or more reaction zones arranged in the direction of flow of the reaction mixture and having separate circulations of heat exchange composition.

10. The process of claim 1, wherein the heat exchanger plates are combined into two or more modules.

11. The process of claim 1, wherein said reactor is cylindrical.

12. The process of claim 1, wherein said reactor is a right parallelepiped.

13. The process of claim 1, wherein the heat exchange composition is an organic liquid.

14. The process of claim 1, wherein the heat exchange composition is an inorganic liquid.

15. The process of claim 1, wherein the heat exchange composition is water.

16. The process of claim 1, wherein the heat exchange plates are arranged spirally in the reactor.

17. The process of claim 1, wherein the heat exchange plates are arranged concentrically in the reactor.

18. The process of claim 1, wherein the heat exchange plates are arranged radially in the reactor.

19. The process of claim 1, further comprising isolating or recovering acrolein.

20. The process of claim 1, further comprising isolating or recovering methacrolein.

21. The process of claim 1, further comprising isolating or recovering acrylic acid.

22. The process of claim 1, further comprising isolating or recovering methacrylic acid.

23. The process of claim 1, wherein said $C_3$ or $C_4$ precursor comprises at least one compound selected from the group consisting of propene, acrolein, tert-butanol, isobutene, isobutene, isobutyraldehyde, methacrolein, isobutyric acid, and methyl tert-butyl ether.

24. The process of claim 1, comprising catalytic gas-phase reaction of propene and/or acrolein at a temperature ranging from 200 to 450° C.

25. The process of claim 1, comprising at least one catalyst selected from the group consisting of oxides of molybdenum, oxides of bismuth and oxides of iron.

26. The process of claim 1, comprising at least one catalyst selected from the group consisting of oxides of molybdenum and oxides of vanadium.

27. The process of claim 1, wherein the heat exchanger composition comprises water and superatmospheric pressure ranges from 20 to 120 bar.

28. The process of claim 1, wherein the heat exchanger composition comprises an inorganic composition which remains in the liquid state or partly or completely vaporized at the reaction temperature of the catalytic gas-phase oxidation.

29. The process of claim 1, wherein the heat exchanger composition comprises an organic composition which remains in the liquid state or partly or completely vaporized at the reaction temperature of the catalytic gas-phase oxidation.

30. The process of claim 1, wherein the heat exchanger composition at least partially vaporizes at the reaction temperature of the catalytic gas-phase oxidation.

* * * * *

UNITED STATES PATENT AND TRADEMARK OFFICE
CERTIFICATE OF CORRECTION

PATENT NO. : 7,253,308 B1
APPLICATION NO. : 10/110229
DATED : August 7, 2007
INVENTOR(S) : Hechler et al.

It is certified that error appears in the above-identified patent and that said Letters Patent is hereby corrected as shown below:

On the title page, Item (54), the Title information is incorrect. Item (54) should read:

-- Item (54) METHOD FOR CATALYTIC GAS PHASE OXIDATION TO (METH) ACROLEIN AND/OR (METH) ACRYLIC ACID --

On the title page, Item (45), the Notice information is incorrect. Item (45) should read:

-- Item (45) Date of Patent: Aug. 7, 2007

(*) Notice: Subject to any disclaimer, the term of this patent is extended or adjusted under 35 U.S.C. 154 (b) by 655 days. --

Signed and Sealed this

Sixteenth Day of October, 2007

JON W. DUDAS
*Director of the United States Patent and Trademark Office*